United States Patent [19]
Green et al.

[11] Patent Number: 4,948,921
[45] Date of Patent: Aug. 14, 1990

[54] PROCESS FOR THE PRODUCTION AND RECOVERY OF TRIMELLITIC ACID

[75] Inventors: Michael R. Green, Geneva; Wayne P. Schammel, Naperville, both of Ill.

[73] Assignee: Amoco Corporation, Chicago, Ill.

[21] Appl. No.: 373,345

[22] Filed: Jun. 29, 1989

[51] Int. Cl.$^5$ ............................................ C07C 51/215
[52] U.S. Cl. .................... 562/413; 549/245; 562/414; 562/416; 562/485; 562/486
[58] Field of Search ............... 562/409, 413, 414, 416, 562/486, 485; 549/245

[56] References Cited

U.S. PATENT DOCUMENTS

| | | | |
|---|---|---|---|
| 2,833,816 | 5/1958 | Saffer et al. | 562/416 |
| 3,161,658 | 12/1964 | Meyer | 562/414 X |
| 3,491,144 | 1/1970 | Ember et al. | 562/413 |
| 4,322,549 | 3/1982 | Kuhlmann et al. | 562/416 |
| 4,398,040 | 8/1983 | Suzuki et al. | 562/413 |
| 4,587,355 | 5/1986 | Brown et al. | 562/414 |
| 4,764,639 | 8/1988 | Schammel | 562/416 |
| 4,816,601 | 3/1989 | Lowry et al. | 562/413 |

Primary Examiner—Werren B. Lone
Assistant Examiner—Vera C. Clarke
Attorney, Agent, or Firm—Gunar J. Blumberg; William H. Magidson; Ralph C. Medhurst

[57] ABSTRACT

A process for the oxidation of pseudocumene to TMLA is disclosed which comprises catalytic oxidation of pseudocumene with air in the presence of acetic acid in an oxidation zone in the liquid phase wherein the weight ratio of acetic acid to pseudocumene is in the range of about 0.5–0:1.0 and the catalyst comprises one or more heavy metal oxidation catalysts comprising zirconium, cobalt, and manganese to provide about 0.1 to about 0.4 weight percent total metals based on pseudocumene and a source of bromine. The addition of the bromine component is controlled to provide a total of about 0.10 to about 0.30 weight percent total bromine based on pseudocumene. The total weight ratio of bromine ions to total metals ions is about 0.5 to about 2.0. The zirconium content is about 1 to about 5% and the manganese content is about 14 to about 60% each by weight of the total metals. The reaction temperature is about 300° F. to about 420° F. The crude trimellitic anhydride is hydrolyzed with water or a mixture of a low molecular weight carboxylic acid and water. Alternatively, a trimellitic anhydride/dimethylformamide adduct is prepared and this adduct is hydrolyzed with a mixture of a low molecular weight carboxylic acid and water. Trimellitic acid is useful in the manufacture of polyesters and polyamide-imides.

17 Claims, No Drawings

PROCESS FOR THE PRODUCTION AND RECOVERY OF TRIMELLITIC ACID

BACKGROUND OF THE INVENTION

This invention relates to a process for manufacture of trimellitic acid from 1,2,4-trimethyl benzene, commonly known as pseudocumene, and more particularly relates to a method of recovering pure trimellitic acid (TMLA) from the reaction mass obtained by the liquid-phase oxidation of pseudocumene by air or oxygen.

The process of this invention provides a commercial process for the manufacture of TMLA through the catalytic liquid phase oxidation of commercially available pseudocumene with air in the presence of acetic acid as reaction solvent, separation and recovery of crystalline trimellitic acid from the oxidation reaction effluent, thermal dehydration of trimellitic acid to its anhydride and hydrolyzing the trimellitic anhydride (TMA) to TMLA with a solvent comprising water or a mixture thereof with one or more low molecular weight carboxylic acids.

This invention further provides a process for the manufacture of pure TMLA where instead of hydrolyzing the TMA to TMLA in water or a mixture of water and one or more low molecular weight carboxylic acids as described above, a TMA/dimethylformamide (DMF) adduct is hydrolyzed. The TMA/DMF adduct is prepared by dissolving TMA in DMF at elevated temperatures and cooling the solution to precipitate a reasonably stable DMF/TMA adduct. This adduct, which is believed to be comprised of one molecule of DMF and one molecule of TMA, is treated with a mixture of water and one or more low molecular weight carboxylic acids to free the TMA in the form of its hydrolyzed product, trimellitic acid.

The following are the general advantages of our novel process, including the ability to improve the TMLA product color as evidenced by TMLA $\Delta E$ values. TMLA has advantages over trimellitic anhydride in that TMLA is not a respiratory sensitizer. Our process improves the TMLA product purity as evidenced by the decrease in the bromine levels and by the decrease in the Esterification Gas Chromatography (EGC) detected impurity level. If the TMLA purity is calculated by difference from the levels of impurities detected by EGC, then it is readily seen that in most cases the TMLA purity produced by our novel process is over 99.0%. The high purity of the TMLA produced by our process will play a significant role in opening up new markets for TMLA, in which a product of 99%+purity is desired. The impurities present in largest concentration in commercial TMLA are the phthalic acids: orthophthalic acid (OA), isophthalic acid (IA) and terephthalic acid (TA). The impurities interfere with the use of TMLA in polymerization and plasticizer manufacture and, consequently, methods to eliminate them from TMLA are desired. Our novel process has accomplished this. Previous research has shown that it is not possible to achieve the separation of IA and TA through fractionation, however, in our novel process a reduction in the level of diacid impurities has been obtained. The main portion of this reduction is by removal of OA and IA. Table IV illustrates some of the advantages of our process.

Qualitative observations indicate that as the percentage of low molecular weight carboxylic acid increases in the hydrolysis solvent the tendency of TMLA to supersaturate in the solvent is decreased. In fact, at a 3 to 1 solvent ratio (solvent to TMA) in 95:5 wt % acetic acid:water, the TMLA actually precipitates out as it hydrolyzes.

Pseudocumene is oxidized with air mainly to a mixture of dimethylbenzoic acids in the presence of catalysis provided only by cobalt and/or manganese oxidation catalysts under liquid phase conditions using acetic acid as the reaction solvent. By the use of oxygen as oxidant and a combination of cobalt as metal oxidation catalyst and alpha-methylenic ketones as side chain oxidation initiators or promoters, pseudocumene is oxidized mainly to a mixture of 2-methylterephthalic acid and 4-methyl isophthalic acid in the presence of acetic acid solvent and under liquid phase conditions at atmospheric pressure. Catalytic liquid phase oxidation of pseudocumene with air can be accomplished in the presence of acetic acid solvent and the catalysis provided by the combination of heavy metal oxidation catalyst and a source of bromine as disclosed and claimed in U.S. Pat. No. 2,833,816. This oxidation method using a combination of heavy metal oxidation catalyst and a source of bromine to provide catalysis results in the production of a 92 weight percent TMLA filter cake product in a two hour reaction at 198° C. (about 390° F.). The theoretical yield of TMLA from pseudocumene is 175 weight percent. However, the oxidation method of U.S. Pat. No. 2,833,816 has been developed to produce total TMLA yields in the range of 152 to 161 weight percent or about 87% to about 92% of theory based on the pseudocumene hydrocarbon feed. By total yield of TMLA is meant all of the TMLA in the oxidation reaction effluent.

Even though the more highly developed catalytic liquid phase air oxidation of pseudocumene by the method of U.S. Pat. No. 2,833,816 produces total trimellitic acid yields of 152 to 161 weight percent based on commercially available pseudocumene, there are also coproduced trimesic acid, iso- and terephthalic acids, 4-methylorthophthalic acid, 2-methylterephthalic acid, 4-methylisophthalic acid and formyl phthalic acids in amounts as to present substantial problems in the recovery of high quality trimellitic acid, dehydration of trimellitic acid to its intramolecular anhydride and recovery of that anhydride.

Another problem in the manufacture of TMLA through the oxidation of pseudocumene to TMLA in the presence of acetic acid comes from the relatively high solubility of TMLA in acetic acid. This solubility goes from about 1.0 pound per 100 pounds glacial acetic acid at 80° F. to 6.5 pounds per 100 pounds glacial acetic acid at 220° F. The presence of water in the acetic acid increases the solubility of TMLA so that in aqueous acetic acid solvent having 82 to 85% acetic acid and 18 to 15% water by weight there are dissolved at 80° and 220° F. about 3.2 pounds and 16.5 pounds TMLA per 100 pounds solvent. Ordinarily aqueous acetic acid of 90 to 98% (10 to 2% water) by weight is used in the oxidation as solvent not only because acetic acid of higher strength is more expensive to recover, but also because the presence of 2 to 10% water by weight substantially eliminates oxidation induction. During oxidation of the methyl groups to carboxylic acid groups water is produced as a by-product and is generally retained through the removal of heat of reaction by condensing the acetic acid and water boil-up from the liquid phase in the oxidation zone and returning as condensate to the oxidation zone. The aqueous acetic acid solvent in the effluent removed from the oxidation zone can contain about 10 to 25% water (90 to 75% acetic acid) by weight when the 90 to 98% aqueous acetic acid solvent is used in the weight ratios of 5 to 2 parts per part of pseudocumene. Thus at usual crystallization temperatures of 60° to 120° F. a substantial amount of trimellitic acid remains in solution.

For example, in Example II of U.S. Pat. No. 3,161,658 there is described the cooling to 100° F. of an oxidation reaction effluent containing for each 500 parts acetic acid solvent 200 parts TMLA and 50 parts of pseudocumene oxidation intermediates. There was recovered 135 parts crystalline TMLA per 500 parts of acetic acid solvent. Thus, of the originally produced 200 parts TMLA there was left in solution 65 parts or 32.5%. This appears to have been an oxidation of pseudocumene conducted in the presence of acetic acid solvent in the ratio of about 3.5 parts solvent per part of pseudocumene. Higher ratios of solvent to pseudocumene would have caused a greater proportion of the total TMLA to remain in solution at 100° F. For example, at a 5 to 1 solvent ratio 45% of the trimellitic acid produced would have remained in solution at crystallization and filtration temperatures of 100° F.

U.S. Patent 3,161,658 provides one technique for recovering the TMLA remaining dissolved in the aqueous acetic acid mother liquor. This is done by adding the mother liquor to a pool of molten TMA (370°–375° F.) and flashing off water and acetic acid vapors and drawing off from the molten pool liquid in an amount equivalent to the weight of solids charged with the mother liquor. This liquid draw off is solidified, ground and dissolved in a dialkyl ketone or aromatic hydrocarbon (the ketone solution must be filtered to remove insolubles) and the solution is combined with anhydride from dehydrated 100° F. filter cake. The aromatic hydrocarbon solution is filtered to remove an insoluble oily residue and the filtrate cooled to 75° F. to precipitate trimellitic anhydride. This anhydride can be added to the anhydride from dehydration of 100° F. first filter cake. By simple flashing at 6 mm Hg absolute there is recovered a trimellitic anhydride product of 95% anhydride content, 95% pure in yields of 85 to 90% based on the trimellitic acid produced by the oxidation. However, the ketone and aromatic hydrocarbon solvents are flammable and their foregoing uses, although advantageous, do present fire hazards.

U.S. Pat. No. 3,096,343 teaches a method for isolating trimellitic acid or trimellitic anhydride. In this method TMA or TMLA is first dissolved in hot DMF to form a solution. This solution is cooled to precipitate a TMA/DMF or TMLA/DMF adduct and the adduct is separated from the remaining solution. The isolated adduct is heated to drive off the DMF leaving the TMA or TMLA. While this patent teaches a method for isolating TMA or TMLA, the patent does not teach or specify the purity levels that can be achieved by the disclosed process. As will be discussed in more detail subsequently, it has been determined that the method disclosed in the U.S. Pat. No. 3,096,343 does not provide TMLA of sufficient purity for modern applications of TMLA and that the process of the instant invention is a superior process in that a more highly pure TMLA is provided.

The intramolecular anhydride of TMLA has become a commercial starting material for surface coatings having the desired properties of high thermal decomposition, high temperature insulating properties and good resistance to chemical attack and are substantially insoluble. These surface coatings are obtained from prepolymers prepared, for example, from TMLA intramolecular anhydrides and polyamines. Because of the trifunctionality of the intramolecular anhydride the final surface coating product is a polyamide-imide. The intramolecular anhydride of TMLA also has become a starting material for solid foams obtained by reacting an isothiocyanate among other reactants with the intramolecular anhydride. Air and heat drying paints and enamels with hydrocarbon or water solvent vehicles are also prepared from the intramolecular anhydride of TMLA. For most of these uses, TMLA intramolecular anhydride of an anhydride purity of 98 to 99% is required.

For many commercial applications mentioned above, color of the TMLA has become an important specification. Highly colored brown, tan, or even yellow products may no longer be acceptable. Triethylene Glycol (TEG) color is a typical standard measure of this performance quality of TMLA. In this method, a reaction of the TMLA with a 300% molar excess of triethylene glycol is carried out at 500° F. (about 260° C.) to produce a solution whose color is matched with APHA color standards. Reaction time is sixty minutes. A typical commercial product must have a TEG color of 170 or less.

The Finished Ester Color (FEC) test is another method for evaluating the color of TMA or TMLA. This test is similar to the TEG test described above, however, instead of preparing an ester of TMA (or TMLA) using triethylene glycol, an ester is prepared using 2-ethylhexanol. The color of the resulting ester is likewise evaluated using the APHA color standards.

A further method for evaluating the color of TMA or TMLA is termed the $\Delta E$ method. This is a spectrophotometric method wherein the total color difference between a solution of 3N NaOH and a solution composed of 5 gm of TMA or TMLA dissolved in 30 ml of 3N NaOH is obtained. The $\Delta E$ value is related to the color of the TMA product in the 400 to 700 nm wavelength range as measured by a spectrophotometer.

The problems that require solving are the recovery of TMLA in yields above 87 to 92 mole percent utilizing catalytic liquid phase oxidation of pseudocumene with air in the presence of acetic acid solvent, the increase of recovery of TMLA from the oxidation reaction effluent, an improved distillative and/or evaporative process for separating the intramolecular anhydride from the crude anhydride melt obtained by the dehydration of impure TMLA, elimination of the fire hazards accompanying the use of dialkyl ketones or aromatic hydrocarbon extract solvents previously disclosed for advantageous use in increasing the recovery of TMLA and the other problems before mentioned. The advantage of our novel process is to hydrolyze the TMA, or the TMA/DMF adduct, with aqueous acetic acid or water and recover pure TMLA which does not have the sensitization effects associated with TMA.

U.S. Pat. No. 4,587,350, incorporated by reference herein, discloses a process for the oxidation of pseudocumene to TMLA by a catalytic oxidation of pseudocumene with air in the presence of acetic acid in an oxidation zone in the liquid phase with catalysts comprising zirconium, cobalt, and manganese and a source of bromine.

The process of this invention provides an integrated system for the commercial production of TMLA.

A process for the manufacture of TMLA by the steps of catalytic oxidation of pseudocumene in the presence of acetic acid in an oxidation zone wherein liquid-phase conditions are maintained and the catalyst comprises one or more heavy metal oxidation catalysts comprising zirconium, cobalt, and manganese and a source of bromine, cooling the oxidation reaction effluent to crystallize TMLA, separating and recovering crystallized TMLA from the acetic acid solvent mother liquor, distilling from the acetic acid mother liquor to obtain a mixture of acetic acid and water for concentration of the acetic acid content to provide acetic acid solvent concentrate for recycle to the oxidation and to obtain a bottoms fraction having high melting solids, heating the crystalline TMLA to convert it to its anhydride and distilling the anhydride to obtain distilled TMA. The improvement arises from hydrolyzing in a mixture of acetic acid or other low molecular weight carboxylic acids and water the TMA to TMLA continuously or in a batch process. The ratio of acetic acid or other low molecular weight carboxylic acid to water is about 0 to about 19; preferably about 1 to about 19 by weight, and most preferably 19. The amount of carboxylic acid and/or water solvent used to hydrolyze the TMA to TMLA is not critical. However a weight ratio of from about 1 to about 10 is useful and a ratio of from about 3 to about 7 is preferred.

Alternatively, it is a TMA/DMF adduct that is treated with a mixture of acetic acid or other low molecular weight carboxylic acid, and water to form the purified TMLA. When purifying TMA this process comprises dissolving trimellitic anhydride (TMA) in hot dimethylformamide (DMF) to form a DMF solution, cooling the DMF solution to precipitate a TMA/DMF adduct, separating the TMA/DMF adduct from the remaining DMF, treating the TMA/DMF adduct with a mixture of acetic acid or other low molecular weight carboxylic acid and water to decompose the TMA/DMF adduct and hydrolyze the TMA to trimellitic acid, and separating the trimellitic acid from the remaining liquid to recover pure trimellitic acid.

The TMA/DMF solution may be first treated with activated carbon and filtered to remove the carbon and any insoluble impurities. In the mixture of the low molecular weight carboxylic acid and water used to decompose the TMA/DMF adduct the ratio of acid to water is about 1 to about 19, preferably about 3 to about 19 by weight. The amount of DMF that is required to dissolve the TMA is not critical. The amount used, however, must be sufficient to dissolve all or most of the TMA at a temperature of from room temperature to the boiling temperature of DMF at atmospheric pressure or if superatmospheric pressures are employed then at the boiling temperature of the DMF at the superatmospheric pressure. There should also be at least enough DMF to provide at least about 1 mole of DMF per mole of the TMA. Preferably the weight ratio of DMF to TMA should be from about 0.3 to about 6 and, preferably, the mixture of TMA and DMF is heated to from about 50 to about 160° C. to dissolve or substantially dissolve the TMA.

The amount of the mixture of low molecular weight carboxylic acid and water required to decompose the TMA/DMF adduct, or the temperature or time required to effect this decomposition are not critical although the preferred method for decomposing the TMA/DMF adduct comprises heating the TMA/DMF adduct with a mixture of the carboxylic acid and water wherein the weight ratio of the mixture of carboxylic acid and water to the TMA/DMF adduct is from about 1 to about 7 and preferably from about 3 to about 5. The temperature for the decomposition preferably is in the range of from about 70° to about 115° and heating is continued for a time sufficient to complete or substantially complete the decomposition of the TMA/DMF adduct and hydrolyze the TMA to TMLA.

The low molecular weight carboxylic acids useful for this invention are those having from 1 to 4 carbon atoms and may be straight chain, branched, saturated or unsaturated. Examples of these carboxylic acids are formic, acetic, propionic, butyric, acrylic, crotonic, isocrotonic, vinylacetic, methyacrylic and isobutyric acid. Due mainly to cost and availability the preferred acids are formic, acetic, and propionic acid. Acetic acid is the most preferred. Mixtures of these acids having 1–4 carbon atoms are also useful.

BRIEF DESCRIPTION OF THE INVENTION

We have discovered an improved process for the manufacture of TMLA by the steps of catalytic oxidation of pseudocumene in the presence of acetic acid in an oxidation zone wherein liquid-phase conditions are maintained and wherein the weight ratio of acetic acid to pseudocumene is in the range of about 0.5:1.0 to about 5.0:1.0 and the catalyst comprises one or more heavy metal oxidation catalysts comprising zirconium, cobalt, and manganese to provide about 0.1 to about 0.4, preferably about 0.22 to about 0.32, weight percent total metals based on pseudocumene and a source of bromine and to provide a total of about 0.10 to about 0.30 weight percent total bromine based on pseudocumene, wherein the total weight ratio of bromine ions to total metal ions is about 0.5 to about 2.0, the zirconium content is about 1 to about 5%, preferably about 2.0 to about 4.0, and the manganese content is about 14 to about 60%, each metal by weight of the total metals and wherein the cobalt content is about 35 to about 80 weight percent, temperatures in the oxidation are in a range of about 220° F. to about 480° F., preferably about 300° F. to about 430° F., cooling the oxidation reaction effluent to crystallize TMLA, separating and recovering crystallized TMLA from the acetic acid solvent mother liquor, distilling from the acetic acid mother liquor to obtain a mixture of acetic acid and water for concentration of the acetic acid content to provide acetic acid solvent concentrate for recycle to the oxidation and to obtain a bottoms fraction having high melting solids, heating the crystalline TMLA to convert it to its anhydride and distilling the anhydride to obtain trimellitic anhydride product which is then hydrolyzed with a solvent comprising water or a mixture thereof with one or more low molecular weight carboxylic acids wherein the low molecular weight carboxylic acids have from 1 to 4 carbon atoms. The ratio of the low molecular weight carboxylic acid to water is about 0 to about 19 preferably about 1 to about 19 by weight. Preferably the low molecular weight carboxylic acid is acetic acid. The crude TMA is purified by distillation at a temperature in the range of about 425° to about 575° F., preferably about 450° to about 550° F., and an absolute pressure of about 5 to about 400 mm. Hg, preferably about 4 to about 300 mm. Hg, and condensing the vaporized overhead fraction to obtain trimellitic anhydride product which is hydrolyzed as described above.

We have also discovered that instead of treating the TMA with water or a mixture of water and one or more low molecular weight carboxylic acids to form pure TMLA as is described in the process above, the TMA can be converted into pure TMLA by dissolving the TMA in dimethylformamide (DMF) at an elevated temperature to form a DMF solution, optionally treating this DMF solution with activated charcoal and filtering the DMF solution to remove the charcoal and insoluble impurities, cooling the DMF solution to precipitate a TMA/DMF adduct, separating the TMA/DMF adduct from the remaining solution, treating the TMA/DMF adduct with a mixture of a low molecular weight carboxylic acid and water to decompose the TMA/DMF adduct and form purified TMLA, and separating the purified TMLA from the mixture of DMF, water and carboxylic acid.

Commercially available pseudocumene is not pure and contains 1 to 5 weight percent of alkyl substituted benzenes having boiling points close to that of pseudocumene such as ethyl toluenes and mesitylene $C_9$ aromatics and even some $C_8$ aromatics such as the xylenes. The ethyl toluenes and xylenes impurities are oxidized to phthalic acids and mesitylene is oxidized to trimesic acid (1,3,5-benzene tricarboxylic acid) at the same time pseudocumene is oxidized to TMLA. It is difficult to convert all of the three methyl groups of pseudocumene to carboxylic acid groups. This difficulty arises from the deleterious effect that conversion of one or two of the methyl groups to carboxylic acid groups has on the remaining methyl group or groups. That oxidation difficulty results in the coproduction of small amounts of 4-methylorthophthalic acid, 2-methylterephthalic acid and 4-methylisophthalic acid. That oxidation difficulty is in addition to the coproduction of such next to last step oxidation by-products as the formylphthalic acids. The last oxidation step product of pseudocumene is TMLA.

We have discovered an improved process for the manufacture of TMLA starting with pseudocumene. The improvement arises from the discovery of a process for recovering TMLA in yields in the range of about 87 to about 94 mol % produced by catalytic liquid phase air oxidation of pseudocumene in the presence of catalysis provided by the combination of heavy metal oxidation catalyst and bromine or a source of bromine and in the presence of acetic acid solvent having 80 to 97% acetic acid and 3 to 20% water by weight. The recovery portion of the process of this invention starts with the effluent from the oxidation process which produces 135 to 161 weight percent or more TMLA based on pseudocumene oxidized with air in the presence of 2 to 5 parts of said 93 to 98% aqueous acetic acid solvent as oxidation reaction effluent. Such oxidation reaction effluents contain 182 to 338 parts aqueous acetic acid of about 10 to about 25% water (90 to 75% acetic acid) per 100 parts TMLA, all by weight. Since the acid recovery technique of this invention is equally applicable, as will be later apparent, to oxidation reaction effluents having aqueous acetic acid solvent of such wide water variations as 10 to 25 weight percent, there is eliminated the need for having precise control over the water content of the solvent initially charged to the oxidation reaction as before thought or appeared to be needed to aid in the separation and recovery of TMLA.

The suspension of crystals formed in the crystallization zone is transferred out as feed for a means for separating solids and liquids. Such solid-liquid separation means as continuous centrifuging, filtering, settling, and the like can be used.

The previously mentioned starting oxidation reaction effluent is obtained by the air oxidation of pseudocumene in the presence of aqueous acetic acid solvent of less than 10 weight percent, preferably 2 to 7 weight percent, water content and in the presence of catalysis provided by the combined use of heavy metal oxidation catalyst and bromine at an oxidation temperature within the range of 300° and 420° F. and a pressure to maintain at least a liquid phase of acetic acid solvent and pseudocumene in the oxidation zone at the operating temperature. Pressures in the range of 100 to 400 psig (pounds per square inch gauge) are satisfactory for maintaining necessary liquid phase conditions in the oxidation zone at said operating temperature. The oxidation can be conducted in a batchwise, semi-continuous or continuous manner. By "semi-continuous" is meant charging solvent and catalyst to an oxidation reactor and heating them to reaction temperature and pressure and then simultaneously introducing pseudocumene and air into the oxidation zone with or without additional components of the catalyst system until all the hydrocarbon has been added (i.e., the continuous portion) and then introducing air with or without catalyst components but not hydrocarbon into the oxidation zone (batchwise portion) until the oxidation of pseudocumene is substantially complete, i.e., oxygen is no longer being consumed. Semi-continuous, then in part combines some features of both continuous and batchwise oxidation. Continuous operation can be conducted in one oxidation zone or in a plurality of series connected oxidation zones, preferably four to six, or in a plug flow manner in a pipeline oxidation reactor having one or more than one inlet for catalyst component and/or air injection.

The precise conditions of operation developed for the high conversion oxidation of pseudocumene to TMLA are not material to the understanding and practice of the present invention. Also those precise operating conditions are not a part of this invention. This invention however does depend and uses to advantage the factual existence of the ability to obtain such high conversions of pseudocumene with air as the oxidant, the use of the system of catalyst provided by the combination of heavy metal oxidation catalyst and bromine as taught in U.S. Pat. No. 2,833,816, the use of acetic acid solvent having 95 to 98% acetic acid and 5 to 2% water by weight and the conditions of temperature and pressure before mentioned for liquid phase operation. This high conversion oxidation, then is the starting process step in the combination of process steps that make the total process for obtaining high purity TMLA in high yields.

For the understanding and practice of the present invention it is necessary to know the amounts of aromatic co-products and by-products also present in the oxidation reaction effluent. These aromatic co-products and by-products have already been specifically identified by types. Most useful for the understanding and practice of this invention is not the precise amount of each specific aromatic co-product and by-product, but rather, the weight ratio of the total of said aromatic by-products and coproducts related to the TMLA present in the oxidation reaction effluent. The total weight of said aromatic coproducts and by-products can be in the ratio range of from 5 to 25 parts per 100 parts of TMLA by weight.

DESIRABLE OPERATING CONDITIONS

Desirable operating conditions for the process steps of this invention are given in the following description. Oxidation reaction effluent is obtained by the oxidation of pseudocumene with air in an oxidation zone at 300 to 420° F. and 100 to 400 psig in the presence of 1.5 to 3.5 parts inclusive of 90 to 98% aqueous acetic acid (10 to 2% water) per part of pseudocumene of 97 to 99% by weight purity in the presence of heavy metals (e.g., supplied as zirconium acetate, and cobalt and manganese acetate tetrahydrates) in a total concentration of 0.06 to 0.30 weight percent as metals and bromide as provided by hydrogen bromide, sodium bromide, and/or tetrabromoethane in a bromide concentration of 0.1 to 0.7 weight percent. The weight percent of catalyst components are based on the acetic acid solvent. The resulting oxidation effluent withdrawn from the oxidation zone is at about 375° to about 400° F. and contains TMLA in an amount equivalent to 1.35 to 1.61 pounds per pound of pseudocumene and aromatic impurities in the range of 5 to 12 pounds per 100 pounds of TMLA.

A slurry of TMLA crystals of from 40 to 60% crystal solids by weight is obtained depending upon the portion of water and acetic acid vaporized and removed from a crystallization zone.

The slurry from the crystallization zone is continuously transferred to a rotary vacuum filter, centrifugal filter, or filter press and TMLA crystal cake is separated at 110° to 130° F. The mother liquor is collected in a surge drum. The filter cake contains 15 to 35% acetic acid.

The acetic acid wet filter cake is continuously charged by screw conveyor to a boiler containing molten crude trimellitic anhydride at about 400° to about 470° F. and pressures in a range of about 10 to 25 psi. The hold time in the boiler is about 1 to 2 hours which is sufficient time to assure removal of acetic acid and dehydrate about 85% of the feed TMLA to its anhydride. Some of the anhydride tends to leave the top of the boiler with the acetic acid vapors. These vapors are transferred to the stripper feed vessel and combined with the mother liquor.

Liquid is withdrawn continuously from the first dehydration zone and fed into the second dehydration zone operated at a temperature in the range of about 400 to about 470° F. and a pressure of about 100 to about 400 mm. Hg.

Liquid is withdrawn continuously from the second dehydration boiler in an amount equivalent in weight to the dry solids content of the wet cake fed to the boiler. This liquid containing crude TMA (3 to 5% impurities) is continuously charged to an anhydride product distillation tower operated at a temperature in a range of about 450° F. to about 500° F. and pressure in a range of about 4 to about 100 mm. Hg absolute pressure. The vapor mixture from either product flasher passes through a hot condenser to condense only the anhydride. The liquid anhydride is cooled to a temperature in the range of about 325° F. to about 375° F. Hg absolute pressure. The materials boiling below TMLA are drawn off as vapors.

The liquid TMA condensate which may be at about 325° F. to about 375° F. is hydrolyzed with a solvent comprising water or a mixture thereof with one or more low molecular weight carboxylic acids and the recovered TMLA is recovered in yields of about 115% to about 135% based on pseudocumene used. The initial temperature of the TMA is, however, not critical.

Alternatively the TMA can be converted into purified TMA by dissolving or substantially dissolving the TMA in dimethylformamide (DMF) at an elevated temperature to from a DMF solution, optionally treating this DMF solution with activated charcoal and filtering to remove the charcoal and any insoluble impurities, cooling the DMF solution to precipitate a TMA/DMF adduct, separating the TMA/DMF adduct from the remaining solution by using separating means well known in the art such as settling, decantation, filtration or centrifugation, treating the TMA/DMF adduct with a mixture comprising a low molecular weight carboxylic acid and water at a temperature and for a time sufficient to decompose the TMA/DMF adduct and hydrolyze the TMA to TMLA and thereby form purified TMLA, and finally separating the purified TMLA from the mixture of DMF, water and low molecular weight carboxylic acid. The following illustrative examples will demonstrate operations of the total process of this invention under prepared executions. In these examples acetic acid was utilized; however, the low molecular weight carboxylic acids having from 1 to 4 carbon atoms or mixtures thereof are also useful.

EXAMPLE 1

This example simply illustrates the product quality improvements that are achieved by hydrolyzing the current TMA product to TMLA in either water or in aqueous acetic acid. The analytical data is summarized in Table I. Color and purity enhancements occur in either solvent, but the data clearly show that aqueous acetic acid is the superior solvent. For the sample hydrolyzed in water, B, the TMLA color as measured by ΔE decreased 43.8% from an initial value of 3.2 units to a final value of 1.8 units. The amount of bromine containing impurities also was reduced significantly. A decrease of 62.7% gas obtained. Product purity gas also improved as evidenced by the decrease (26.8%) in the level of EGC detected impurities.

For comparison, the sample hydrolyzed in 95:5 wt % acetic acid:water yielded a superior TMLA product. Relative to the initial starting material, Sample A, the ΔE color was decreased 62.5%, the bromine level was reduced by 72.1%, and the amount of EGC detected impurities decreased by 41.3%.

TABLE I

| Sample ID | A | B | C |
|---|---|---|---|
| Solvent | (none) | 95 wt % HOAc/5 wt % $H_2O$ | $H_2O$ |
| Solvent Ratio (TMA:Solvent) | — | 1:3 | 1:3.4 |
| ΔE | 3.2 | 1.2 | 1.8 |
| Br (ppm) | 161 | 45 | 60 |
| EGC Results (wt %) | | | |
| Benzoic Acid | 0.013 | <0.01 | <0.01 |
| OA | 0.177 | 0.019 | 0.030 |
| TA | 0.502 | 0.487 | 0.462 |
| IA | 0.487 | 0.234 | 0.408 |
| 4-MeOA | 0.014 | <0.01 | <0.01 |
| Other Low Boilers | 0.346 | 0.257 | 0.371 |
| Trimesic Acid | 0.011 | <0.01 | <0.01 |
| 1,2,3,4-tetra-carboxybenzene | 0.207 | 0.033 | 0.023 |
| 1,2,4,5-tetra-carboxybenzene | 0.288 | 0.098 | 0.096 |
| Other High Boilers | 0.167 | 0.171 | 0.229 |

TABLE I-continued

| Sample ID | A | B | C |
|---|---|---|---|
| EGC Detected Impurties | 2.212 | 1.299 | 1.619 |

EXAMPLE 2

In this example a comparison similar to Example 1 is made, however, a higher quality TMA starting material is used. In addition, the TMLA samples prepared were analyzed by the finished ester color (FEC) test, which measures the color properties of the ester, tris(2-ethylhexyl)trimellitate, obtained by reacting TMA with 2-ethylhexanol. The analytical data is summarized in Table II.

Relative to the initial starting material, Sample D, the sample hydrolyzed in water, Sample E, yielded a 37.9% decrease in the TMLA ΔE color, a 61.4% reduction in the bromine level, and a 49.3% decrease in the amount of EGC detected impurities. Most significantly, this example shows that the color improvement obtained in the TMLA product also occurs for the resulting tris(2-ethylhexyl)trimellitate. A decrease of 33.3% in the FEC was obtained.

For comparison, the sample hydrolyzed in 95:5 wt % acetic acid:water yielded a superior TMLA product and a less colored tris(2-ethylhexyl)trimellitate. Relative to the initial starting material, Sample D, the TMLA ΔE color was decreased 75.4%, the bromine level was reduced by 84.9%, and the amount of EGC detected impurities was decreased by 60.6%. Further the FEC was decreased by 50%.

TABLE II

| Sample ID | D | E | F |
|---|---|---|---|
| Solvent | | $H_2O$ | 95 wt % HOAc/5 wt % $H_2O$ |
| Solvent Ratio (TMA: Solvent) | | 1:3 | 1:3 |
| ΔE | 2.64 | 1.64 | 0.65 |
| FEC (APHA) | 30 | 20 | 15 |
| Br (ppm) | 166 | 64 | 25 |
| EGC Results (wt %) | | | |
| OA | 0.171 | 0.077 | 0.015 |
| TA | 0.343 | 0.190 | 0.312 |
| IA | 0.275 | 0.229 | 0.090 |
| 4-MeOA | 0.057 | 0.034 | <0.01 |
| 2-MeTA | 0.014 | <0.01 | 0.012 |
| Other Low Boilers | 0.301 | 0.156 | 0.095 |
| Trimesic Acid | 0.012 | <0.01 | <0.01 |
| 1,2,3,4-tetra-carboxybenzene | 0.105 | <0.01 | 0.012 |
| 1,2,4,5-tetra-carboxybenzene | 0.169 | 0.045 | 0.034 |
| Other High Boilers | 0.038 | 0.022 | 0.015 |
| EGC Detected Impurities | 1.485 | 0.753 | 0.585 |

EXAMPLE 3

This example illustrates the effect of solvent ratio (weight solvent to weight TWA) on the hydrolysis reaction. The data clearly shot that changes in the solvent ratio do not lead to substantial changes in the TWLA product quality relative to changes in solvent composition. The analytical data for this example are given in Table III.

Relative to the initial starting material, Sample G, the samples hydrolyzed in water, Sample H (solvent ratio=7) and Sample J (solvent ratio=3), yielded decreases of 30.7% and 33.4% in the TMLA ΔE color, decreases of 55.4% and 53.5% in the bromine level, and decreases of 37.7% and 33.6% in the amount of EGC detected impurities, respectively.

For comparison, the samples hydrolyzed in 95:5 wt % acetic acid:water, Sample I (solvent ratio =7 and Sample K (solvent ratio =3), yielded superior TMLA product. Relative to the initial starting material, Sample G, the TMLA ΔE colors were decreased 80.4% and 73.0%, the bromine levels were reduced by 82.8% and 73.9%, and the amount of EGC detected impurities was decreased by 65.7% and 60.4%, respectively.

TABLE III

| Sample ID | G | H | I | J | K |
|---|---|---|---|---|---|
| Solvent Composition[1] | | 100 | 5 | 100 | 5 |
| Solvent Ratio[2] | | 7 | 7 | 3 | 3 |
| ΔE | 3.26 | 2.26 | 0.64 | 2.17 | 0.88 |
| Br (ppm) | 157 | 70 | 27 | 73 | 41 |
| EGC Detected Impurities (Weight Percent) | | | | | |
| Benzoic Acid | 0.014 | <0.01 | <0.01 | <0.01 | <0.01 |
| OA | 0.129 | 0.037 | <0.01 | 0.052 | 0.011 |
| TA | 0.426 | 0.454 | 0.387 | 0.421 | 0.387 |
| IA | 0.383 | 0.401 | 0.081 | 0.379 | 0.132 |
| 4-MeOA | 0.019 | <0.01 | <0.01 | 0.010 | <0.01 |
| Other Low | 0.172 | 0.031 | <0.01 | 0.057 | <0.01 |
| Trimesic Acid | 0.011 | <0.01 | <0.01 | <0.01 | <0.01 |
| 1,2,3,4-tetra-carboxybenzene | 0.157 | 0.022 | <0.01 | 0.025 | 0.015 |
| 1,2,4,5-tetra-carboxybenzene | 0.203 | <0.01 | 0.043 | 0.058 | 0.052 |
| Other High Boilers | 0.026 | 0.014 | 0.017 | 0.020 | 0.013 |
| Total EGC Detected Impurities | 1.540 | 0.959 | 0.528 | 1.022 | 0.610 |

[1]Weight percent water in acetic acid.
[2]Weight solvent to weight TMA.

EXAMPLE 4

This example demonstrates the large changes that occur in TMLA product quality as the hydrolysis solvent composition is changed from 100% water to 95:5 wt % acetic acid:water. The analytical data is summarized in Table IV.

The data in Table IV clearly show that TMLA product color gradually improves until the hydrolysis solvent contains 50 wt % acetic acid. The optimum range for TMLA product color and purity lies between 50 to 95 weight percent acetic acid.

TABLE IV

| Sample ID | L | M | N | O | P | Q | S |
|---|---|---|---|---|---|---|---|
| Solvent Composition[1,2] | 0 | 12.5 | 25.0 | 37.5 | 50.0 | 75.0 | 95.0 |
| ΔE | 1.90 | 1.75 | 1.57 | 1.42 | 0.91 | 0.87 | 1.10 |
| Br(ppm) | 65 | 60 | 52 | 48 | 30 | 36 | 45 |
| EGC Detected Impurities (Weight Percent) | | | | | | | |
| OA | 0.044 | 0.041 | 0.030 | 0.024 | 0.011 | 0.010 | 0.017 |

TABLE IV-continued

| Sample ID | L | M | N | O | P | Q | S |
|---|---|---|---|---|---|---|---|
| TA | 0.430 | 0.390 | 0.509 | 0.488 | 0.468 | 0.371 | 0.400 |
| IA | 0.362 | 0.342 | 0.342 | 0.307 | 0.185 | 0.128 | 0.169 |
| Unidentified Low Boilers | 0.046 | 0.017 | 0.039 | <0.01 | 0.011 | 0.012 | 0.036 |
| TME | 0.011 | <0.01 | <0.01 | <0.01 | <0.01 | <0.01 | <0.01 |
| 1,2,3,4-tetra-carboxy-benzene | 0.021 | <0.01 | <0.01 | <0.01 | <0.01 | 0.022 | 0.040 |
| 1,2,4,5-tetra-carboxy-benzene | 0.066 | 0.056 | 0.049 | 0.069 | 0.044 | 0.052 | 0.086 |
| Other High Boilers | 0.034 | 0.016 | 0.016 | 0.018 | 0.016 | 0.012 | 0.01 |
| Total EGC Detected Impurities | 1.014 | 0.862 | 0.985 | 0.906 | 0.735 | 0.607 | 0.758 |

[1]Weight percent acetic acid in water.
[2]Solvent ratio = 3.

EXAMPLE 5

The following example illustrates the undesirable results that are obtained when TWA is purified by the method of forming a TMA/DMF adduct and then thermally decomposing the TMA/DMF adduct to obtain TMA.

One hundred grams of TMA were combined with two hundred grams of DMF. The resulting mixture was heated to 90° C. to dissolve all of the TMA. The solution was poured into a beaker, covered, and allowed to stand overnight to crystallize. The next morning the 1:1 TMA:DMF adduct was isolated from solution by vacuum filtration. The crystals were then placed in a vacuum oven at 121° C overnight to dry. A viscous liquid was obtained the next morning, which solidified upon cooling to room temperature. The composition was determined by esterification gas chromatography (ECG). ECG analysis showed the material to contain 11.914 wt. % impurities, which is a highly impure TMLA product.

EXAMPLE 6

The following example demonstrates that the process of this invention provides highly pure TMLA and that the decomposition of the TMA/DMF using the process of this invention is greatly improved over the thermal process of Example 5.

The 1:1 TMA:DMF adduct was prepared as described in Example 5, however, the adduct was dried at 70° C. overnight in a vacuum oven. Fifty grams of the TMA:DMF adduct were then combined with 150 grams of 95:5 wt. % acetic acid:water. The resulting mixture was heated to reflux and held for 15 minutes. The resulting slurry was poured into a beaker and allowed to crystallize at room temperature overnight. The crystals were isolated the next morning by vacuum filtration and dried in a vacuum oven at 70° C overnight. The resulting TMLA crystals were analyzed for color by the ΔE procedure and for purity by ECG. The results obtained are listed in Table V under Sample U along with a comparison to the original TMA starting material, Sample T. This table demonstrates that TMLA prepared by the process of this invention is highly pure. Relative to the TMA starting material, the color is improved by more than 2 ΔE units and impurities are reduced from 1.485% to only 0.031% as measured by EGC. It is apparent from this data that the process of the instant invention is greatly superior to the process used in Example 5.

TABLE V

| Sample ID | T | U |
|---|---|---|
| ΔE | 2.64 | 0.47 |
| EGC Results (wt %) | | |
| OA | 0.171 | <0.01 |
| TA | 0.343 | <0.019 |
| IA | 0.275 | <0.01 |
| 4-MeOA | 0.057 | <0.01 |
| 2-MeTA | 0.014 | <0.01 |
| Other Low Boilers | 0.301 | 0.012 |
| Trimesic Acid | 0.012 | <0.01 |
| 1,2,3,4-tetra-carboxybenzene | 0.105 | <0.01 |
| 1,2,4,5-tetra-carboxybenzene | 0.169 | <0.01 |
| Other High Boilers | 0.169 | <0.01 |
|  | 0.038 | <0.01 |
| EGC detected impurities | 1.485 | 0.031 |
| Purity by Diff. | 98.515 | 99.969 |

We claim:

1. A process for oxidizing pseudocumene to trimellitic acid which comprises catalytic oxidation of pseudocumene with air in the presence of acetic acid in an oxidation zone wherein liquidphase conditions are maintained and wherein the weight ratio of acetic acid to pseudocuene is in the range of about 0.5–4.0:1.0 and the catalyst comprises one or more heavy metal oxidation catalysts comprising zirconium, cobalt, and manganese to provide about 0.1 to about 0.4 weight percent total metals based on pseudocumene and a source of bromine and to provide a total about 0.10 to about 0.30 weight percent total bromine based on pseudocumene, wherein the total weight ratio of bromine ions to total metal ions is about 0.5 to about 2.0, the zirconium content is about 1 to about 5% and the manganese content is about 14 to about 60%, each metal by weight of the total metals and wherein the cobalt content is about 35 to about 80 weight percent, the temperature in the last 40% of the oxidation is upward from about 350° F. to about 420° F., the temperature in the preceding stage is between about 300° F. and about 350° F., cooling the oxidation reaction effluent to crystallize crude trimellitic acid, separating acid recovering crystallized crude trimellitic acid from the acetic acid solvent mother liquor, heating the crystallized crude trimellitic acid to convert it to its anhydride and distilling the anhydride to obtain trimellitic anhydride product, and wherein the resulting trimellitic anhydride product is hydrolyze with a solvent comprising water or a mixture thereof with one or more low molecular weight carboxylic acids wherein the log molecular weight carboxylic acid contains 1 to 4 carbon atoms to obtain pure trimellitic acid.

2. The process of claim 1 wherein the ratio of the low molecular weight carboxylic acid to water in said solvent is about 0 to about 19 by weight.

3. The process of claim 1 wherein said solvent is a mixture of water and low molecular weight carboxylic acid selected from the group consisting of formic acid, acetic acid, propionic acid and mixtures thereof.

4. The process of claim 1 wherein said solvent comprises a mixture of water and acetic acid.

5. The process of claim 4 wherein the weight ratio of acetic acid to water is from about 1 to about 19.

6. The process of claim 4 wherein the weight ratio of acetic acid to water is 19.

7. The process of claim 1 which comprises a process for the oxidation of pseudocumene with molecular oxygen to trimellitic acid under liquid-phase conditions in the presence of a zirconium-cobalt-manganese-bromine catalyst wherein the molecular ratio of zirconium to cobalt is about 1:10 to about 1:50 at a temperature in the range of about 300° F. to about 420° F., which process comprises conducting a semicontinuous oxidation of the pseudocumene so that only one methyl moiety on the average on the benzene ring is converted to the carboxylic acid group, thus avoiding the positioning of the catalyst and completing the reaction in a noncontinuous process at a temperature of about 340° F. to about 420° F.

8. The process of claim 7 wherein about 10 to about 20% of the filtrate saturated with trimellitic acid is pumped back to the crystallizer section to provide pumpability of the trimellitic acid slurry while maintaining a recovery of trimellitic acid by the filter over 90 mole percent.

9. A process for oxidizing pseudocumene to trimellitic acid which comprises catalytic oxidation of pseudocumene with air in the presence of acetic in an oxidation zone wherein liquid-phase conditions are maintained and wherein the weight ratio of acetic acid to pseudocumene is in the range of about 0.5–4.0:1.0 and the catalyst comprises one or more heavy metal oxidation catalysts comprising zirconium, cobalt, and manganese to provide about 0.1 to about 0.4 weight percent total metals based on pseudocumene and a source of bromine and to provide a total of about 0.10 to about 0.30 weight percent total bromine based on pseudocument, wherein the total weight ratio of bromine ions to total metals ions is about 0.5 to about 2.0, the zirconium content is about 1 to about 5% and the manganese content is about 14 to about 60%, each metal by weight of the total metals and wherein the cobalt content is about 35 to about 80 weight percent, the temperature in the last 40% of the oxidation is upward from about 350° F. to about 420° F., the temperature in the preceding stage is between about 300° F. and about 350° F., cooling the oxidation reaction effluent to crystallize crude trimellitic acid, separating and recovering crystallized crude trimellitic acid from the acetic acid solvent mother liquor, heating the crystallized crude trimellitic acid to convert it to its anhydride and distilling the anhydride to obtain trimellitic anhydride product, and wherein the resulting trimellitic anhydride is purified by dissolving said trimellitic anhydride product in hot dimethylformamide to form a dimethylformamide solution, cooling the dimethylformamide solution to precipitate a trimellitic anhydride/dimethylformamide adduct, separating the trimellitic anhyride/dimethylformamide adduct from the remaining dimethylformamide, treating the trimellitic anhydride/dimethylformamide adduct with a mixture comprising a low molecular weight carboxylic acid having 1 to 4 carbon atoms and water to decompose the trimellitic anhydride/dimethylformamide adduct and hydrolyze the trimellitic anhydride to trimellitic acid, and separating the trimellitic acid from the remaining liquid to recover pure trimellitic acid.

10. The process of claim 9 wherein said low molecular weight carboxylic acid is selected from the group consisting of formic acid, acetic acid, propionic acid and mixtures thereof.

11. The process of claim 9 wherein said low molecular weight carboxylic acid comprises acetic acid.

12. The process of claim 9 wherein the dimethylformamide solution is treated with activated carbon and filtered to remove the activated carbon and any insoluble impurities.

13. The process of claim 9 wherein the treating of the trimellitic anhydride/dimethylformamide adduct with a mixture of low molecular weight carboxylic acid and water to decompose the trimellitic anhydride/dimethylformamide adduct and hydrolyze the trimellitic anhydride to trimellitic acid is at a temperature of from about 70° C. to about 115° C. for a time sufficient to decompose the trimellitic anhydride/dimethylformamide adduct and hydrolyze the trimellitic anhydride to trimellitic acid and wherein the weight ratio of the mixture of low molecular weight carboxylic acid and water to the trimellitic anhydride/dimethylformamide adduct is from about 1 to about 7.

14. The process of claim 9 wherein the ratio of low molecular weight carboxylic acid to water in the mixture of the low molecular weight carboxylic acid and water is from about 1 to about 19 by weight.

15. The process of claim 9 wherein the ratio of the low molecular weight carboxylic acid to water in the mixture of the low molecular weight carboxylic acid and water is from about 3 to about 19 by weight.

16. The process of claim 9 wherein the weight ratio of dimethylformamide to trimellitic anhydride in the dimethylformamide solution is from about 0.3 to about 6.

17. The process of claim 16 wherein the dimethylformamide is heated to from about 50 to about 160° C. to dissolve or substantially dissolve the trimellitic anhydride to form a dimethylformamide solution.

* * * * *

UNITED STATES PATENT OFFICE
CERTIFICATE OF CORRECTION

Patent No. 4,948,921                    Dated  August 14, 1990

Inventor(s) Michael R. Green & Wayne P. Schammel

It is certified that error appears in the above-identified patent and that said Letters Patent is hereby corrected as shown below:

| Col. | Line | |
|---|---|---|
| Abs. | 6 | "0.5-0:1.0" should read --0.5-4.0:1.0-- |
| 8 | 64 | "coproducts" should read --co-products-- |
| 8 | 66 | "coproducts" should read --co-products-- |
| 10 | 40 | "gas" should read --was-- |
| 10 | 40 | "gas" should read --was-- |
| 10 | 47 | "72.1" should read --72.1-- |
| 12 | 1 | "shot" should read --show-- |
| 12 | 3 | "TWLA" should read --TMLA-- |
| 12 | 34 | "Other Low" should read --Other Low Boilers-- |
| 14 | 40-41 | "0.169" <0.01" should read --0.169 <0.01-- |
| 14 | 51 | "liquidphase" should read --liquid-phase-- |
| 14 | 53 | "pseudocuene" should read --pseudocumene-- |
| 15 | 7 | "hydrolyze" should read --hydrolyzed-- |
| 15 | 10 | "log" should read --low-- |
| 15 | 36 | "positioning" should read --poisoning-- |
| 15 | 48 | "acetic in" should read --acetic acid in-- |
| 16 | 15 | "anhyride" should read --anhydride-- |

Signed and Sealed this

Twenty-ninth Day of October, 1991

Attest:

HARRY F. MANBECK, JR.

*Attesting Officer*                    Commissioner of Patents and Trademarks